(12) United States Patent
Eguchi et al.

(10) Patent No.: US 10,130,357 B2
(45) Date of Patent: Nov. 20, 2018

(54) INSTRUMENT FOR DELIVERING A SURGICAL THREAD (71) Applicant: Nagasaki University, Nagasaki-shi, Nagasaki (JP)

(72) Inventors: Susumu Eguchi, Nagasaki (JP); Tamotu Kuroki, Nagasaki (JP); Taiichiro Kosaka, Nagasaki (JP); Takakazu Ishimatu, Nagasaki (JP); Syunji Moromugi, Nagasaki (JP)

(73) Assignee: Nagasaki University, Nagasaki-shi, Nagasaki (JP)

( * ) Notice: Subject to any disclaimer, the term of this patent is extended or adjusted under 35 U.S.C. 154(b) by 114 days.

(21) Appl. No.: 15/129,698

(22) PCT Filed: Mar. 26, 2015

(86) PCT No.: PCT/JP2015/059331
§ 371 (c)(1),
(2) Date: Sep. 27, 2016

(87) PCT Pub. No.: WO2015/147146
PCT Pub. Date: Oct. 1, 2015

(65) Prior Publication Data
US 2017/0128062 A1 May 11, 2017

(30) Foreign Application Priority Data

Mar. 28, 2014 (JP) ................. 2014-067291

(51) Int. Cl.
*A61B 17/04* (2006.01)
*A61B 17/06* (2006.01)
(Continued)

(52) U.S. Cl.
CPC ...... *A61B 17/0485* (2013.01); *A61B 17/0469* (2013.01); *A61B 17/06066* (2013.01);
(Continued)

(58) Field of Classification Search
CPC ......... A61B 17/04; A61B 17/06; A61B 17/12; A61B 17/0485; A61B 17/06109;
(Continued)

(56) References Cited

U.S. PATENT DOCUMENTS 4,013,080 A * 3/1977 Froning ............. A61B 17/3401
604/165.01
5,501,692 A 3/1996 Riza
(Continued)

OTHER PUBLICATIONS

Jun. 9, 2015—International Search Report—Intl App PCT/JP2015/059331.

*Primary Examiner* — Victor Nguyen
(74) *Attorney, Agent, or Firm* — Banner & Witcoff, Ltd.

(57) ABSTRACT

To reduce the risk of damaging organs in a body while delivering a thread during surgery, an instrument for delivering a surgical thread has a grip, an outer cylinder fixed the grip, a hollow needle extending inside the outer cylinder and being configured to be moved relative to the outer cylinder in an axial direction and a loop configured to be housed in the outer cylinder. An end of the outer cylinder is bent in a state where force is not applied. The hollow needle is exposed from the outer cylinder when puncturing skin or etc., and the hollow needle is housed in the outer cylinder when it travels near organs which should not be damaged.

8 Claims, 8 Drawing Sheets

(51) Int. Cl.
*A61B 17/12* (2006.01)
*A61B 17/00* (2006.01)
(52) U.S. Cl.
CPC .. *A61B 17/06109* (2013.01); *A61B 17/12009* (2013.01); *A61B 2017/00309* (2013.01); *A61B 2017/00331* (2013.01); *A61B 2017/00358* (2013.01); *A61B 2017/061* (2013.01); *A61B 2017/06071* (2013.01); *A61B 2017/06095* (2013.01)
(58) Field of Classification Search
CPC .......... A61B 17/0469; A61B 17/06066; A61B 17/3401; A61B 17/06606; A61B 17/12009; A61B 2017/061; A61B 2017/00331
See application file for complete search history.

(56) References Cited

U.S. PATENT DOCUMENTS

| | | | |
|---|---|---|---|
| 5,746,752 A | 5/1998 | Burkhart | |
| 2013/0116709 A1* | 5/2013 | Ziniti | A61B 17/0469 606/144 |
| 2013/0165955 A1 | 6/2013 | Chin | |

* cited by examiner

INSTRUMENT FOR DELIVERING A SURGICAL THREAD

TECHNICAL FIELD

The present invention relates to an instrument for delivering a surgical thread such as ligature inside a body during surgery.

BACKGROUND ART

In recent years, instead laparotomy, surgeries to make a hole on the abdomen, to insert treatment instruments in an abdominal cavity and to treat have come to be performed. For example, Non-Patent Document 1, laparoscopic percutaneous extraperitoneal closure for pediatric inguinal hernia (LPEC method) is disclosed.

This LPEC method is a method for the treatment of inguinal hernia which is the most common disease in pediatric surgery. In LPEC method, a ligature transport instrument that can push-out and pull-in a loop of metal wire at the end thereof is used. After inserting the end of the ligature transport instrument into the abdominal cavity of the patient and moving the ligature along the hernia gate, while the loop at the end of the ligature transport instrument is closed to secure the ligature, then the loop is spread and the ligature transport instrument is pulled out while the ligature is left in the patient's body. The ligature transport instrument is inserted again and is moved along one side of the hernia gate where the ligature does not remain, the ligature that has been left is grasped by closing the loop at the end of the ligature transport instrument and is pulled outside the patient's body.

PRIOR ART DOCUMENTS

Patent Document

[Patent Document 1] Japanese Patent Application Publication Hei 5-42161
[Patent Document 2] Japanese Patent Application Publication Hei 10-146342
[Patent Document 3] Japanese Patent Application Publication Hei 6-54855

Non-Patent Document

[Non-Patent Document 1] Iwade, et. al., "Laparoscopic Percutaneous Extraperitoneal Closure for Inguinal Hernia in Girls at Nagano Children's Hospital", Shinshu Igaku Zasshi, Vol. 61, No. 3, pp. 139-147, June 2016, Shinshu Igakukai

SUMMARY OF THE INVENTION

Problems to be Solved

In case that inguinal hernia is treated by LPEC method, during a movement near a hernia sac or along a hernia gate, vas deferens, testicular artery, vein and femoral vein, etc. can be damaged by the tip of the needle.

Therefore, an object of this invention is to reduce the risk of damaging organs in a body while delivering a surgical thread such as a ligature during surgery.

Means for Solving the Problems

According to an aspect of the present invention, there is provided an instrument for delivering a surgical thread, the instrument comprising: a grip; an outer cylinder fixed the grip; a hollow needle extending inside the outer cylinder and being configured to be moved relative to the outer cylinder in a direction of an axis; and a loop configured to be housed in the hollow needle, wherein an end of the outer cylinder is bent in a state where force is not applied, an bending rigidity in a bending direction of the outer cylinder is smaller than that of the hollow needle, and an bending rigidity in a direction perpendicular to the bending direction is larger than that enables to peel off peritoneum from extra peritoneal tissue by rotating around the axis.

Advantages of the Invention

According to the present invention, it is possible to reduce the risk of damaging organs in a body while delivering a surgical thread during surgery.

EMBODIMENT

Hereinafter, embodiments of an instrument for delivering a surgical thread according to the present invention will be described with reference to the drawings. The following embodiments are just examples, and the present invention is not limited to these. The same symbols are given to same or similar configurations, and duplicated description may be omitted.

First Embodiment

Figure 1:
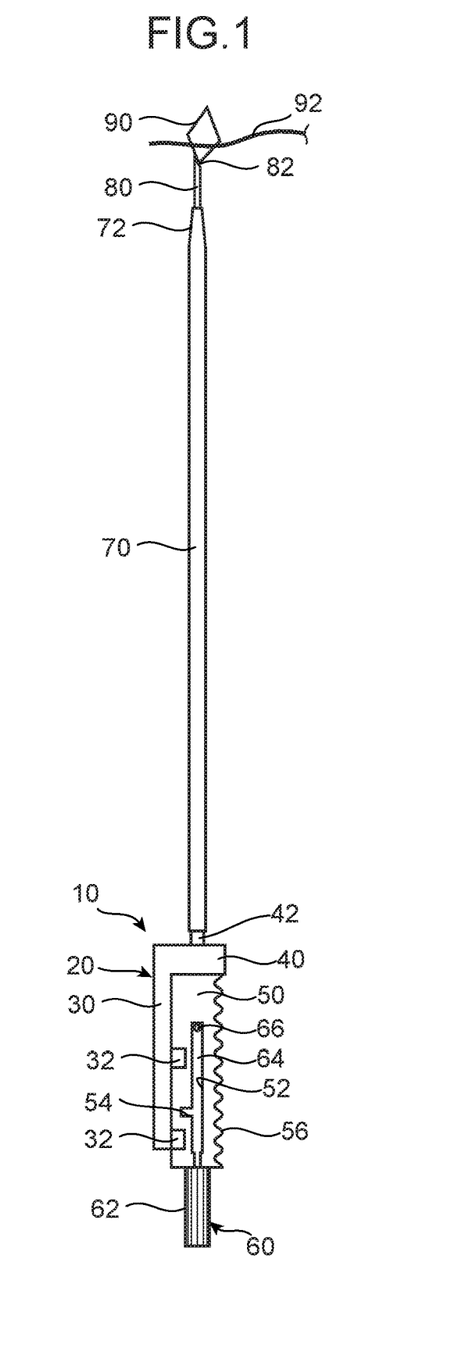
FIG. 1 is a side view of an instrument for delivering a surgical thread according to a first embodiment of the present invention.
Figure 2:
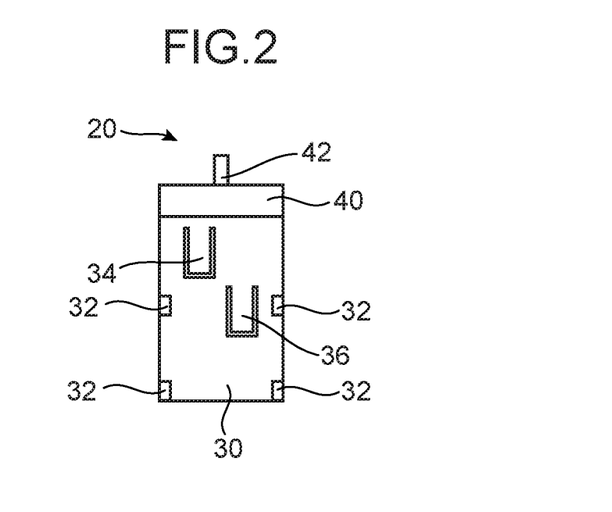
FIG. 2 is a plan view of a base of the instrument for delivering a surgical thread according to a first embodiment of the present invention.

FIG. 1 is a side view of an instrument for delivering a surgical thread according to a first embodiment of the present invention. FIG. 2 is a plan view of a base of the instrument for delivering a surgical thread according to the present embodiment. In FIG. 1, a ligature 92 is also shown.

An instrument for delivering a surgical thread according to this embodiment includes a grip 10, a hollow needle 80, a loop 90, and an outer cylinder 70. The grip 10 includes a base 20, a needle position adjustor 50, and a loop opening and closing portion 60.

The base 20 has a rectangular flat plate portion 30, and a rising portion 40 which rises in the normal direction of the flat plate portion 30 at one short side of the flat plate portion 30. The flat plate portion 30 has two guides 32 projecting in the same direction as the rising portion 40 in two positions each of the two long sides. Further, the flat plate portion 30 has a first rachet 34 and a second rachet 36 located at the two positions where the distances from the rising portions 40 are different. The first rachet 34 and the second rachet 36 are both biased in the protruding direction of the rising portion 40.

A projecting portions 42 projecting in parallel to the surface of the flat plate portion 30 is provided at the roughly center on the side, which is opposite to the flat plate portion 30, of the rising portion 40. A through hole penetrating roughly center of the rising portion 40 and the projecting portion 42 is formed.

The needle position adjustor 50 is formed in a substantially rectangular solid, and is arranged so that one surface is facing to the guide 32 of the flat plate portion 30. Inside the needle position adjustor 50, a cylindrical cavity is formed. On the side of the needle position adjustor 50, a slit 52 is formed. The slit 52 extends in the longitudinal direction of the needle position adjustor 50. And, the side surface of the needle position adjustor 50, a catch 54 communicating with the slit 52 is formed. The catch 54 extends in a direction substantially perpendicular to the slit 52. In order to facilitate preventing slipping when gripped by fingers and sliding operation of the needle position adjustor 50 which is described later, grooves in the short-side direction of the flat plate portion 30 are formed on a surface 56 located on the side of the needle position adjustor 50 opposite to the flat plate portion 30.

The loop opening and closing portion 60 has a handle 62 and a shaft 64. The shaft 64 is inserted into the cavity of the needle position adjustor 50. The handle 62 is fixed to the end of the shaft 64 opposite to the rising portion 40. A hooking protrusion 66 that is slightly smaller than the width of the slit 52 and the catch 54, is provided on the side of the shaft 64.

The outer cylinder 70 is fixed to the projecting portion 42 of the base 20. And, the outer cylinder 70 extends parallel to the longitudinal direction of the flat plate portion 30 of the base 20.

The hollow needle 80 extends inside the outer cylinder 70. The tip 82 of the hollow needle 80, has a sharp shape obtained by cutting a cylinder at an angle. An end of the grip 10 proximal to the hollow needle 80 is fixed to the needle position adjustor 50. The loop 90 is formed in a shape, such as a diamond, so as to be stored in the hollow needle 80 and so as that the ligature pass therethrough.

The base 20 of the grip 10, the needle position adjustor 50 and the loop opening and closing portion 60 is made of resin, for example. The hollow needle 80 is made of metal, for example. The outer cylinder 70 has flexibility and is made of a material that is soft enough to avoid damaging organs in the human body, such as resin. The loop 90 is made of metal wire, for example.

The needle position adjustor 50 is provided slidably in a straight line in the direction of the hollow needle 80 while it is regulated by the guide and remain contacted to one surface of the flat plate portion 30 of the base 20. The loop opening and closing portion 60 is provided slidably in a straight line in the direction of the hollow needle 80 along the interior of the cavity of the needle position adjustor 50.

Figure 3:
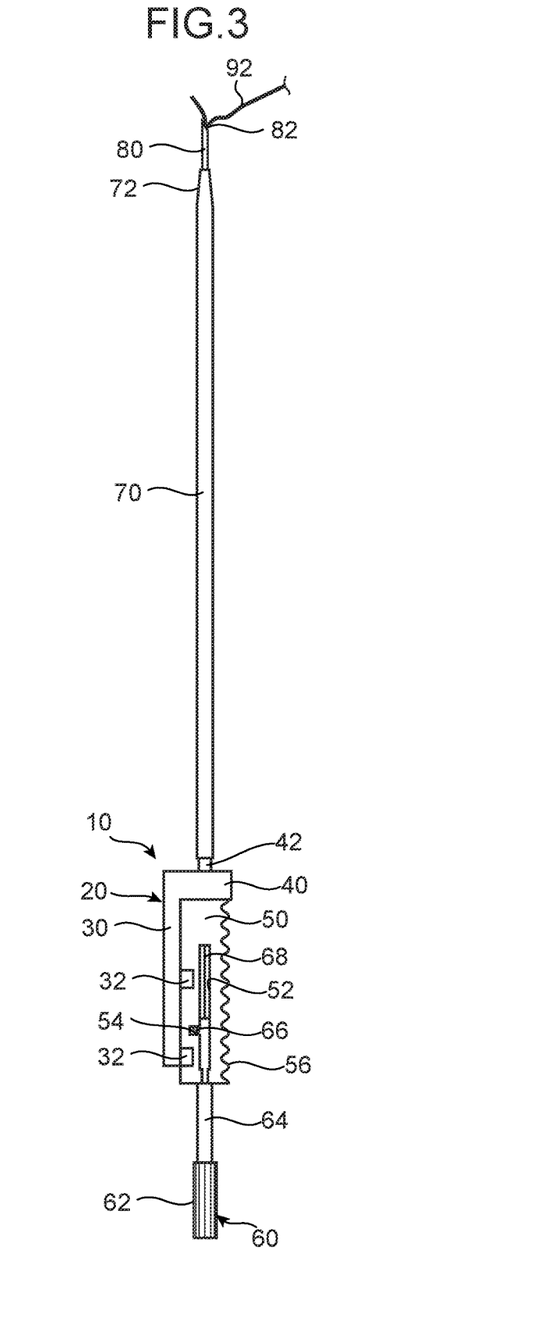
FIG. 3 is a side view of the instrument for delivering a surgical thread according to a first embodiment of the present invention, in a state that the loop opening and closing portion 60 is pulled out.

FIG. 3 is a side view of the instrument for delivering a surgical thread according to the present embodiment, in a state that the loop opening and closing portion 60 is pulled out. In FIG. 3, a ligature 92 is also shown.

Pulling out the loop opening and closing portion 60, in other words, sliding the loop opening and closing portion 60 to the opposite end against the hollow needle 80 so as to separate from the needle position adjustor 50 results in that the wire 68, extending inside the hollow needle 80 from the end of the shaft 66 of the loop opening and closing portion 60 opposite to the handle 62 to the loop 90, is pulled toward the grip 10 and the loop 90 is drawn into the hollow needle 80 from the tip 82 of the hollow needle 80. The loop 90 drawn inside the hollow needle 80 is deformed to a shape with a width of about the inner diameter of the hollow needle 80. If the ligature 92 is pass through the loop 90 in advance, pulling the loop 90 inside the hollow needle 80 results in drawing the loop 90 inside of the hollow needle 80 so as to sandwich the ligature 92. As a result, ligatures 92 will not fall off from the loop 90.

In a state that the loop 90 inside the hollow needle 80, by rotating the handle 62 of the loop opening and closing portion 60 and fitting the hooking protrusion 66 to the catch 54 formed on the side surfaces of the needle position adjustor 50, because the wire 68 cannot be moved relative to the hollow needle 80, the possibility that the ligature 92 falling out from the loop 90 decreases significantly.

Figure 4:
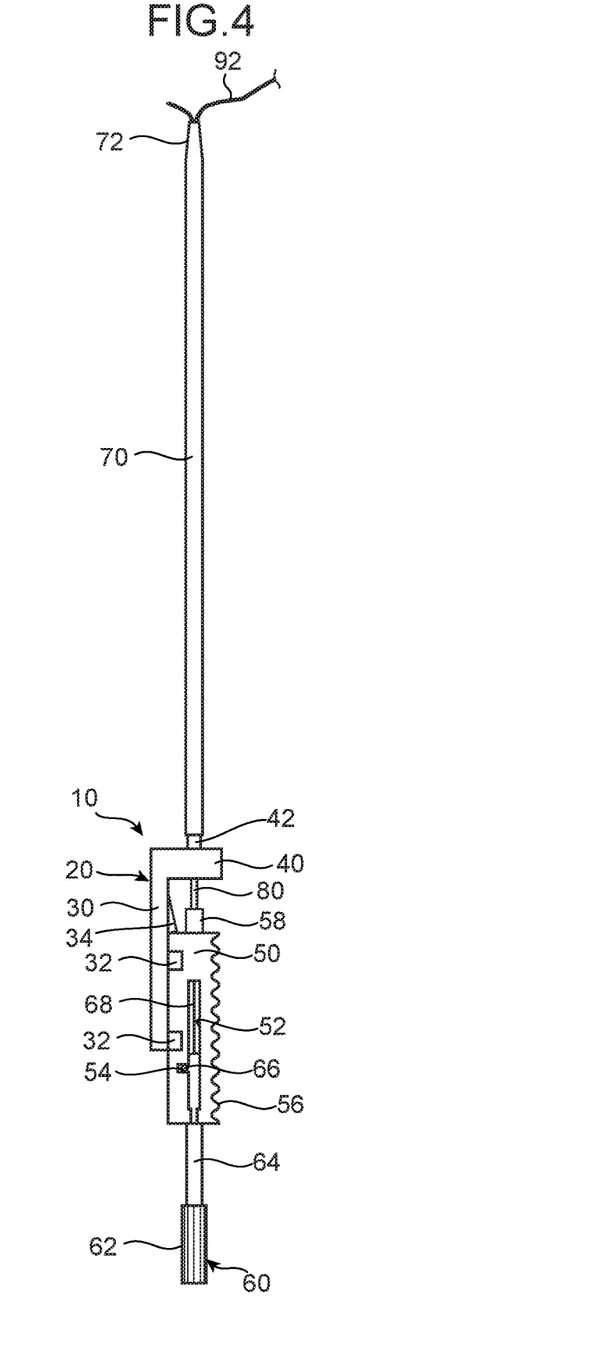
FIG. 4 is a side view of the instrument for delivering a surgical thread according to a first embodiment of the present invention, in a state that the needle position adjustor is pulled out to the first position.

FIG. 4 is a side view of the instrument for delivering a surgical thread according to the present embodiment, in a state that the needle position adjustor is pulled out to the first position. In FIG. 4, a ligature 92 is also shown.

Pulling out the needle position adjustor 50, in other words, sliding the needle position adjustor 50 relative to the base 20 to the opposite end against the outer cylinder 70 so as to separate from the rising portion 40 results in that the tip of the first rachet jumps up after passing through the first rachet and the needle position adjustor 50 come to be immobile toward the rising portion 40. This position will be referred to as first stage.

Drawing the needle position adjustor 50 to the first stage, the hollow needle 80 fixed to a needle fixing portion 58 of the needle position adjustor 50 is moved toward the direction of the grip 10 relative to the outer cylinder 70 and is housed in the inside of the outer cylinder 70. In the situation that the needle position adjustor 50 is drawn to the first stage, the tip 82 of the hollow needle 80 will be located in the vicinity of the end 72 of the outer cylinder 70. Therefore, the outer cylinder 70 remains in a shape substantially along the hollow needle 80, i.e., a linear shape.

The needle fixing portion 58 is formed in a cylindrical shape for example, and the wire 68, which is fixed to the shaft 64 of the loop opening and closing portion 60, extends inside of it relatively movably. On the side of the rising portion 40 of the base 20 facing the needle position adjustor 50, a recess (not shown) configured to be fitted with needle fixing portion 58 is formed. If pushing the needle position adjustor 50 toward the rising portion 40 while the first rachet is pushed to the flat plate portion 30, the needle fixing portion 58 is fitted to the recess formed on the rising portion 40 and the hollow needle 80 is less likely to move relative to the outer cylinder 70.

Figure 5:
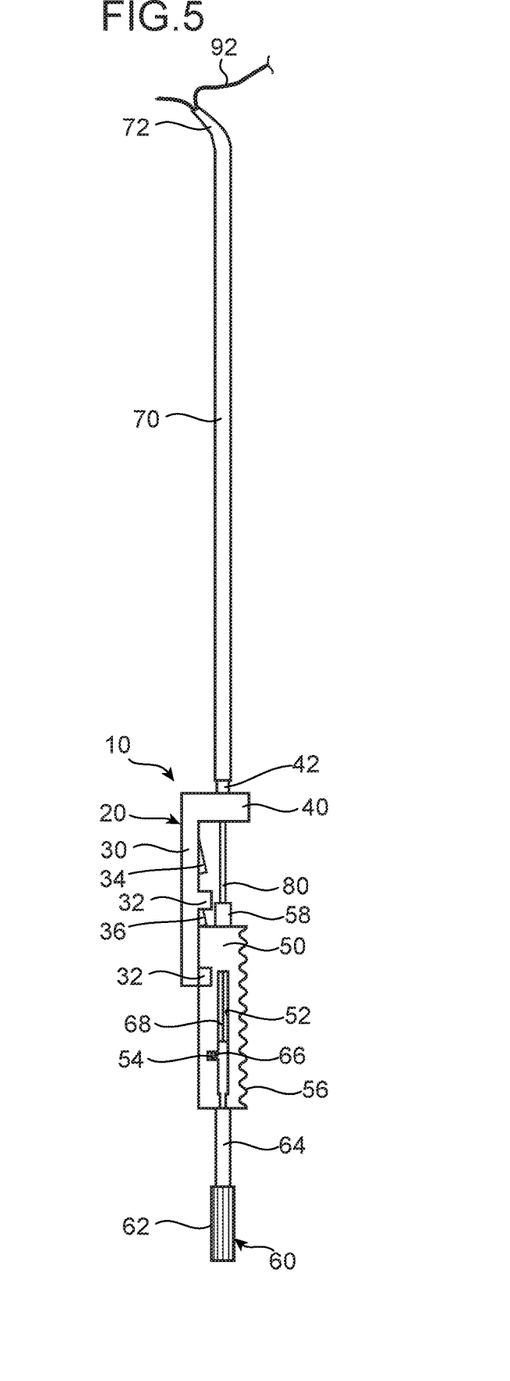
FIG. 5 is a side view of the instrument for delivering a surgical thread according to a first embodiment of the present invention, in a state that the needle position adjustor is pulled out to the second position.

FIG. 5 is a side view of the instrument for delivering a surgical thread according to the present embodiment, in a state that the needle position adjustor is pulled out to the second position. In FIG. 5, a ligature 92 is also shown.

Pulling the needle position adjustor 50 further from the first stage, in other words, sliding the needle position adjustor 50 relative to the base 20 so as to be separated more from the rising portion 40 than the first stage results in that the tip of the second rachet jumps up after passing through the second rachet and the needle position adjustor 50 comes to be immobile toward the rising portion 40. This position will be referred to as second stage.

Drawing the needle position adjustor 50 to the second stage, the hollow needle 80 fixed to the needle fixing portion 58 of the needle position adjustor 50 is housed further inside of the outer cylinder 70 comparing to the first stage. As a result, the distal part of the outer cylinder 70 from the grip 10 farther than the end of the hollow needle 80 is not a shape along the hollow needle 80 but a shape when the force is not applied. In this embodiment, the end 72 of the outer cylinder 70 is in a bent shape with respect to the direction of the hollow needle 80 extending when a force is not applied. Therefore, when the needle position adjustor 50 is pulled out to the second stage, the end 72 of the outer cylinder 70 bends.

Next, a method of operation of inguinal hernia with an instrument for delivering a surgical thread according to the present embodiment will be described.

Figure 6:
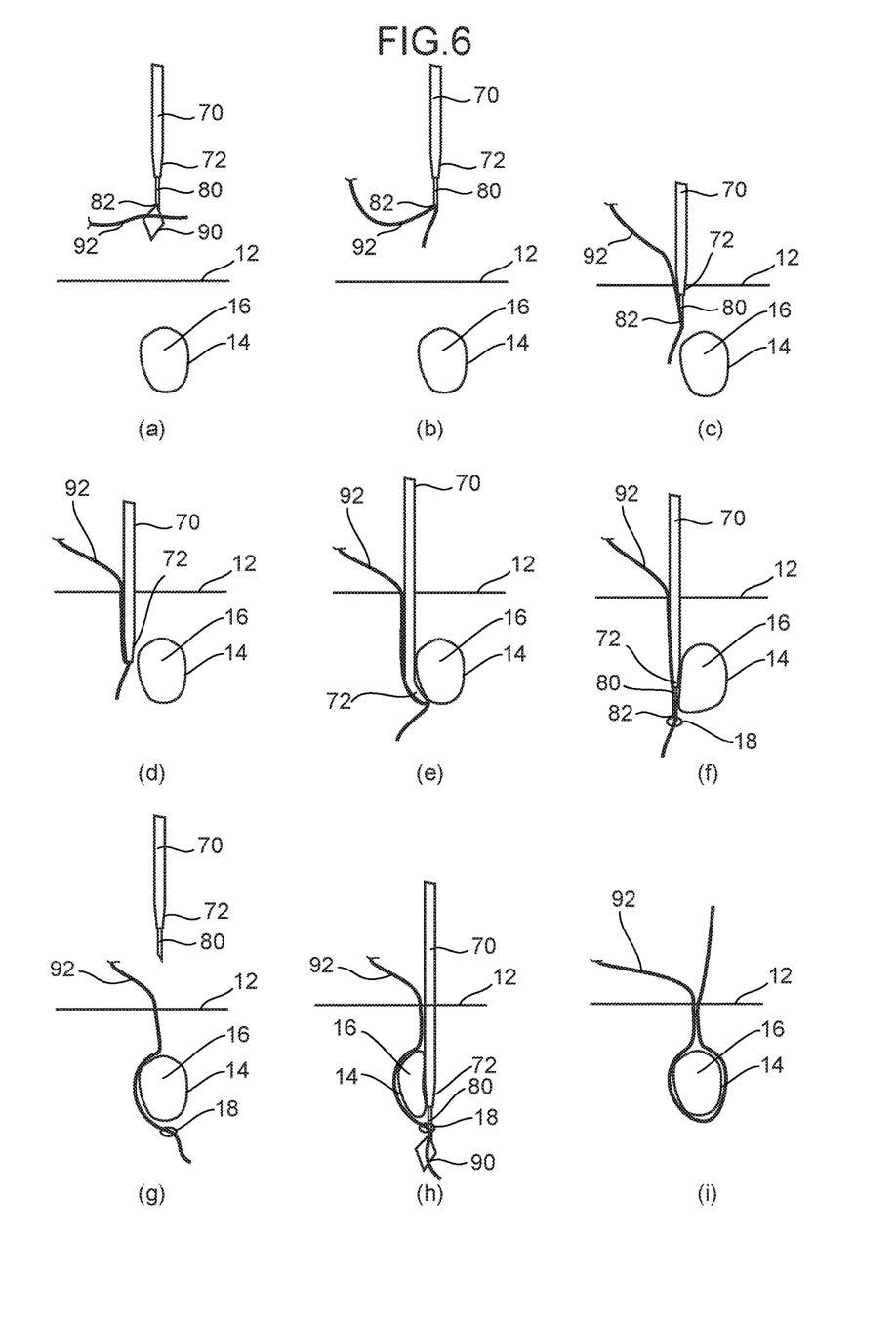
FIG. 6 is a schematic cross sectional view of the diseased part in each stage of the operation of the inguinal hernia with the instrument for delivering a surgical thread according to a first embodiment of the present invention.

FIG. 6 is a schematic cross sectional view of the diseased part in each stage of the operation of the inguinal hernia with the instrument for delivering a surgical thread according to the present embodiment. According to the procedure of surgery, before reaching the state of FIG. 6, an pneumoperitoneum by injecting gas into the abdominal cavity is performed and a laparoscope for observation (not shown) and a grasping forceps (not shown) are inserted into the abdominal cavity.

First, as shown in FIG. 6 (*a*), the loop 90 of the instrument for delivering a surgical thread is opened, and the ligature 92 is passed through the loop 90. At this time, the tip 82 of the hollow needle 80 is kept exposed from the end 72 of the outer cylinder 70. The ligature 92 is a non-absorbable yarn.

Next, as shown in FIG. 6 (*b*), the loop 90 is closed to retain the ligature 92 to the tip 82 of the hollow needle 80. In a state in which the ligature 92 is held at the tip 82 of the hollow needle 80, as shown in FIG. 6 (*c*), the skin 12 is punctured by the tip 82 of the hollow needle 80, and the hollow needle 80 and the outer cylinder 70 is inserted in to the body through the skin and the fascia. Before puncturing the skin 12 by the hollow needle 80, a small incision may be formed.

Thereafter, the needle position adjustor 50 is pulled out to the first stage, as shown in FIG. 6 (*d*), the hollow needle 80 is housed into the outer cylinder 70. In this state, the end 72 of the outer cylinder 70 is transported to the vicinity of the hernia gate 14. If the risk that the tip 82 of the hollow needle 80 damage organ in the body is small, the tip 82 of the hollow needle 80 may out from the outer cylinder 70 while transporting.

After the end 72 of the outer cylinder 70 reaches the vicinity of the hernia gate 14, the needle position adjustor 50 is pulled out to the second stage and the tip 82 of the hollow needle 80 is further moved to the inside of the outer cylinder 70. Thus, as shown in FIG. 6 (*e*), the end 72 of the outer cylinder 70 bends. In this state, the end 72 of the outer cylinder 70 is transported along the hernia gate 14 outside the peritoneum. As a result, the ligature 92 will extend along the hernia gate 14.

The end 72 of the outer cylinder 70 has a portion farther from the axis of the hollow needle 80 than the farthest part of the portion covering the hollow needle 80. Here, the farthest part of the portion covering the hollow needle 80 is the outer periphery of the linear portion of the outer cylinder 70. And, the portion farther from the axis of the hollow needle 80 than the farthest part of the portion covering the hollow needle 80 is the bent tip 72. As described above, the end 72 of the outer cylinder 70 has a rigidity enough to penetrate between the peritoneum and the extra peritoneal tissue even in the absence of the hollow needle 80 therein. If it has the rigidity of this extent, the portion farther from the axis of the hollow needle 80 than the farthest part of the portion covering the hollow needle 80 peels off the peritoneum from the extra peritoneal tissue by pivoting the end 72 of the outer cylinder 70 around the axis of the outer cylinder 70. By transporting while peeling off the peritoneum from the extra peritoneal tissue by the outer cylinder 70 softer than the hollow needle 80, the operation time can be reduced while preventing damage.

After the end 72 of the outer cylinder 70 has reached the farthest point of the hernia gate 14, i.e., in the state that the ligature 92 surrounds nearly half of the hernia gate 14, the needle position adjustor 50 is pushed until it comes to contact with the rising portion 40 of the base 20 and the hollow needle 80 is exposed from the outer cylinder 70. In this state, the hollow needle 80 punctures into the abdominal cavity. Then, the loop 90 is opened by operating the loop opening and closing portion 60, and as shown in FIG. 6 (*f*), the distal end portion of the ligature 92, that has passed through the punctured portion 18, is left in the abdominal cavity. Thereafter, as shown in FIG. 6 (*g*), while the distal end portion of the ligature 92 is left in the abdominal cavity, the hollow needle 80 and the outer cylinder 70 are drawn outside the body. When drawing out the hollow needle 80 to the outside of the body together with the outer cylinder 70, because the sharp portion of the tip 82 of the hollow needle 80 does not move toward the direction in which the sharp portion is pointed, a possibility that the tip 82 hurts the organ in the body is small and so the hollow needle 80 may be moved in the state that it is exposed from the outer cylinder 70.

Next, after the hollow needle 80 is inserted into the skin 12 again in the vicinity of the puncture portion of the skin 12 as shown in FIG. 6 (*c*), the outer cylinder 70 is moved from the puncture portion 18 into the abdominal cavity on the side of the hernia gate 14 opposite to the side where the ligature 92 is left. Here, the hollow needle 80 and the outer cylinder 70 are drawn outside the body, but they may be moved without drawing out on the side of the hernia gate 14 opposite to the side where the ligature 92 is left.

Thereafter, as shown in FIG. 6 (h), the distal end of the ligature 92 left in the abdominal cavity is passed through the loop 90. After the ligature 92 is passed through the loop 90, the loop 90 is housed in the hollow needle 80 and the ligature 92 is fixed at the tip 82 of the hollow needle 80.

After that, by drawing the hollow needle 80 out of the body together with the outer cylinder 70, the end of the ligature 92 is to come out of the body. When drawing out the hollow needle 80 to the outside of the body together with the outer cylinder 70, because the sharp portion of the tip 82 of the hollow needle 80 does not move toward the direction in which the sharp portion is pointed, a possibility that the tip 82 hurts the organ in the body is small and so the hollow needle 80 may be moved in the state that it is exposed from the outer cylinder 70.

After the Ligature 92 travelling around almost of the hernia gate, by ligating the ligature 92 in a state in which the intra-abdominal organs has not been caught in the hernia sac 16, the hernia gate is reefed. In this way, it is possible to ligate the hernia sac. In the above procedure, the movement of the hollow needle 80 and the outer cylinder 70 is performed while confirming the position by the laparoscope (not shown). The operation of removing and passing the ligature 92 from or through the loop 90 is carried out by using a grasping forceps (not shown).

The instrument for delivering a surgical thread according to the present embodiment has the outer cylinder 70 for housing the hollow needle 80. Therefore, by housing the hollow needle 80 into the outer cylinder 70 if necessary, the risk of damaging internal organs by the tip 82 of the hollow needle 80 becomes small. In particular, in the treatment of inguinal hernias, the risk of damaging vas deferens, testicular artery, vein, and femoral vein, etc. is reduced.

Further, the hollow needle 80 can be fixed at the position where the tip 82 is near the end 72 of the outer cylinder 70 (first stage) and the position where the tip 82 is rearward position than the end 72 of the outer cylinder 72 (second stage). In addition, the end 72 of the outer cylinder 70 is flexible has, and is bent in a state where force is not applied. Thus, the end 72 of the outer cylinder 70 can be in a shape suitable for moving by pulling the tip 82 to the first stage if the straight line movement is required and by pulling the tip 82 to the second stage if the curved movement along the hernia gate is required.

Figure 7:
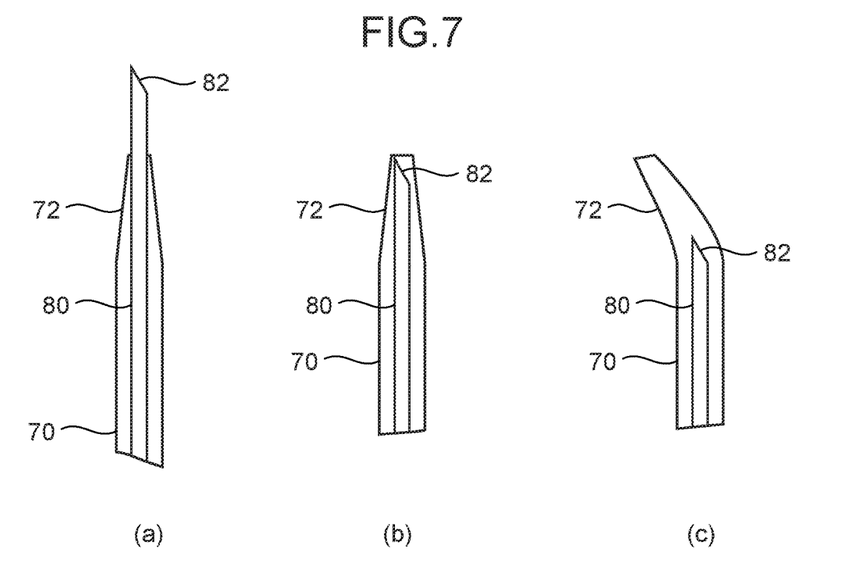
FIG. 7 is a cross sectional view of the instrument for delivering a surgical thread according to a first embodiment of the present invention, (a) in a state that the hollow needle is exposed from the outer cylinder, (b) in a state that the tip of the hollow needle is located at the end of the outer cylinder, and (c) in a state that the tip of the hollow needle is pulled into the outer cylinder.

FIG. 7 is a cross sectional view of the instrument for delivering a surgical thread according to the present embodiment, (a) in a state that the hollow needle is exposed from the outer cylinder, (b) in a state that the tip of the hollow needle is located at the end of the outer cylinder, and (c) in a state that the tip of the hollow needle is pulled into the outer cylinder.

As shown in FIG. 7, the tip 82 of the hollow needle 80 is slanted relative to the direction in which the hollow needle 80 extends. Further, as shown in FIG. 7 (c), the end 72 of the outer cylinder 70 is bent in a state in which no excessive force. Bending direction of the end 72 of the outer cylinder 70 is the direction from the obtuse portion to the sharp portion of the tip 82 of the hollow needle 80. In other words, the tip 82 of the hollow needle 80 has an end face obtained by cutting a cylinder diagonally in the bending direction of the outer cylinder 70, i.e., an end face along the bending direction. By maintaining the relationship of the bending direction of the end 72 of the outer cylinder 70 and the tip 82 of the hollow needle 80 as the relationship described above, during the movement of the hollow needle 80 pulling out from the outer cylinder 70, as shown in FIG. 7 (c) to FIG. (a) via FIG. (b), the risk that the sharp edge of the tip 82 of the hollow needle 80 contacts inner surface of the outer cylinder 70 and damages the outer cylinder 70 is reduced.

It is preferable that the radius of curvature of the bending of the end 72 of the outer cylinder 70 is a size along the traveling direction of the end 72. For example, in the case of inguinal hernia, assuming the diameter of 1 cm, which is a common size of the hernia gate 14, the radius of curvature may be about 5 mm. Preparing those of various radius of curvature, it may be selected in accordance with the patient.

The radius of curvature of bending of the end 72 may not be constant. For example, the distal portion may have a smaller radius of curvature, and the radius of curvature may gradually increase toward the proximal portion. In the present embodiment, the tip 82 of the hollow needle 80 configured to be drawn and fixed at top positions of the first stage and the second stage, however, it is possible to vary the whole of the bending by changing the drawn and fixed position if multi-stage drawing and fixing may be realized by increasing the positions and the end 72 of the outer cylinder 70 having the gradually increasing radius of the curvature is utilized.

In this embodiment, the first rachet 34 and the second rachet 36 are used for drawing and fixing, however the way of fixing is not limited thereto. For example, it may be fixed at any position by friction restraining by pressing the needle position adjustor 50 to the flat portion 30.

If the outer cylinder 70 is formed of semitranslucent resin, it may be difficult to visually recognize the outer cylinder 70 in the laparoscope image during surgery. So, the outer cylinder 70 can be colored. It is preferable that the color of the outer cylinder 70 is a color that can be clearly distinguished from the organs of the body. By keeping at least the end 72 of the outer cylinder the easy-recognizing color while viewed with the laparoscope, it is easy to distinguish from the tissue of the body for example and the travelling position can be more appropriate. The whole of the outer cylinder 70 may be the same color throughout, but the end 72 for example may be colored in a different color from the rest. For example, the whole of the outer cylinder 70 may be made as semi-transparent and only the end 72 may be colored.

In this embodiment, it is describe that the case of the instrument for delivering a surgical thread is used in surgery for inguinal hernia, but it may be used for delivering surgical yarn inside the body during other surgery.

Second Embodiment

Figure 8:
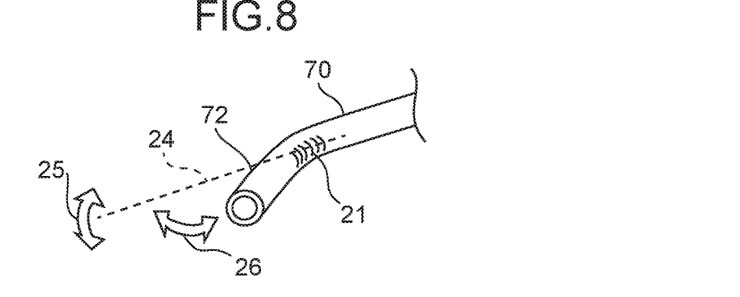
FIG. 8 is a partially enlarged perspective view of an instrument for delivering a surgical thread according to a second embodiment of the present invention.
Figure 9:
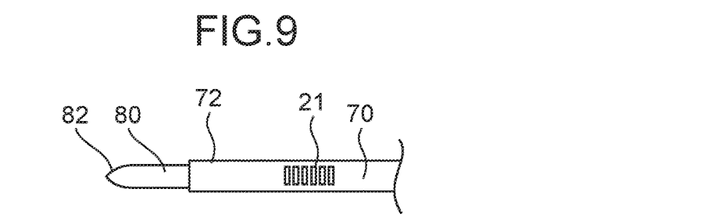
FIG. 9 is a side view of the instrument for delivering a surgical thread according to a second embodiment of the present invention, in a state that the hollow needle is exposed from the outer cylinder.

FIG. 8 is a partially enlarged perspective view of an instrument for delivering a surgical thread according to a second embodiment of the present invention. FIG. 9 is a side view of the instrument for delivering a surgical thread according to the present embodiment, in a state that the hollow needle is exposed from the outer cylinder.

The instrument for delivering a surgical thread according to the present embodiment is different from the first embodiment in the shape of the outer cylinder 70. Slits 21 are formed on the side surface of the outer cylinder 70 in the present embodiment. The slits 21 are formed on the inner side in a state where the end 72 of the outer cylinder 70 is bent. The slits 21 are formed to have a certain length in the axial direction 24 of the outer cylinder 70.

The formation of the slits 21 makes it easy to bent the end 72 of the outer cylinder 70 in a direction 26 that is a direction of bending from the axial direction 24 when a force is not applied and difficult to bent in a direction 25 that is perpendicular to the direction 26 that is a direction of bending of the end 72 from the axial direction 24. In other words, the bending rigidity of the end 72 of the outer cylinder 70 is small in the bending direction 26 and is large in the direction 25 perpendicular to the bending direction 26. As a result, it is hard to bend the end 72 of the outer cylinder 70 in the direction of which rotates about the axis direction 24, i.e., the bending rigidity of the tip 72 of the outer cylinder 70 in the bending direction 26 is small and the torsional rigidity around the axial direction 24 is large. Increasing the torsional rigidity of the end 72 of the outer cylinder 70 makes it easy to peel off the peritoneum from the extra peritoneal tissue.

If the bending rigidity becomes too large together with the torsional rigidity by using hard material or increasing the wall thickness uniformly, the hollow needle 80 would be bent by the outer cylinder 70. If the bending rigidity of the bending direction 26 becomes too large, it may be unable to rectify the bending of the outer cylinder 70 to straight by insertion of the hollow needle 80. However, as the present embodiment, by reducing the rigidity in the bending direction 26 of the outer cylinder 70, the plastic deformation of the hollow needle 80 by the outer cylinder 70 can be suppressed. As a result, it is possible to reduce the burden on the patient's body by reducing the outer diameter or the wall thickness of the hollow needle 80.

Figure 10:
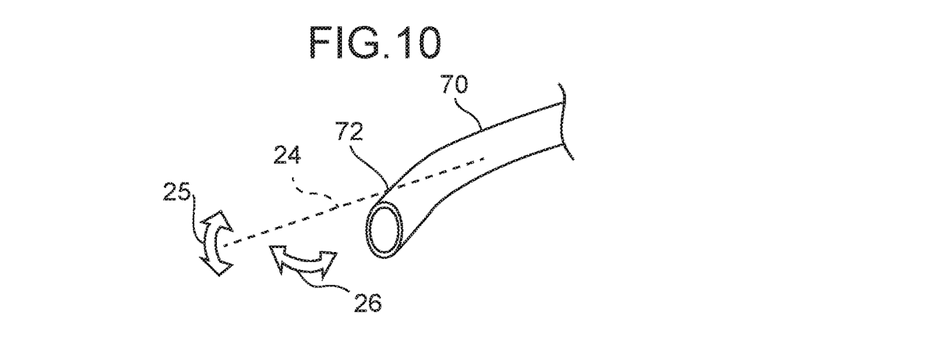
FIG. 10 is a partially enlarged perspective view of an instrument for delivering a surgical thread according to an alternative of a second embodiment of the present invention.
Figure 11:
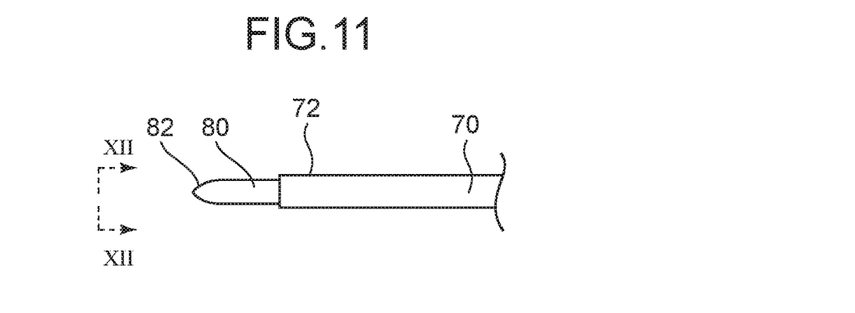
FIG. 11 is a side view of the instrument for delivering a surgical thread according to an alternative of a second embodiment of the present invention, in a state that the hollow needle is exposed from the outer cylinder.
Figure 12:
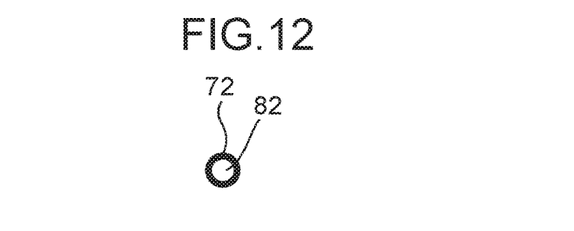
FIG. 12 is a cross sectional view viewed from the arrow XII-XII of the FIG. 11.

FIG. 10 is a partially enlarged perspective view of an instrument for delivering a surgical thread according to an alternative of the present embodiment. FIG. 11 is a side view of the instrument for delivering a surgical thread according to the alternative of the present embodiment, in a state that the hollow needle is exposed from the outer cylinder. FIG. 12 is a cross sectional view viewed from the arrow XII-XII of the FIG. 11.

In this alternative, the outer cylinder 70 has an elliptical cross-section. The ellipse of the cross-section of the outer cylinder 70 has the minor axis parallel to the bending direction 26. As a result, the bending rigidity of the end 72 of the outer cylinder 70 is small in the bending direction 26 and is large in the direction 25 perpendicular to the bending direction 26.

The outer cylinder 70 has the hardness of an extent of which it will be rectified the bending to straight and rectified to a substantially perfect circle along the outer periphery of the hollow needle 80 by exposing the hollow needle 80.

Figure 13:
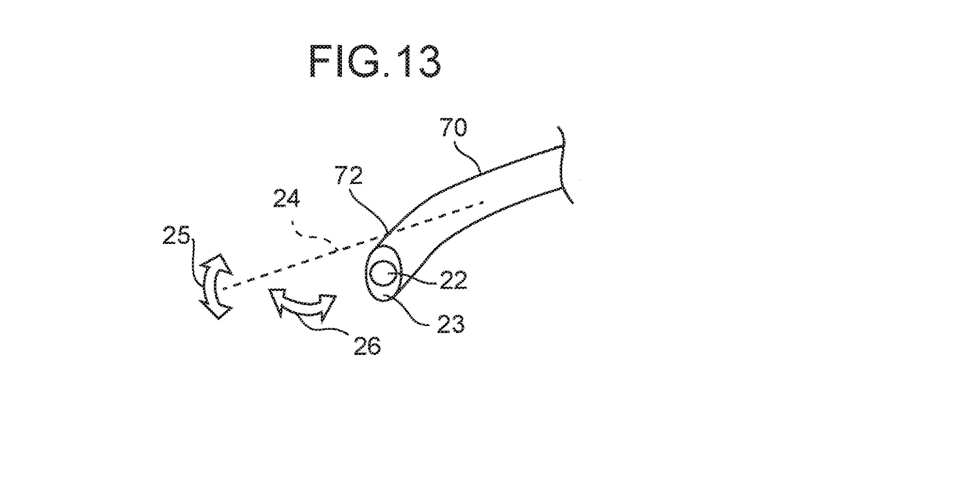
FIG. 13 is a partially enlarged perspective view of an instrument for delivering a surgical thread according to another alternative of a second embodiment of the present invention.

FIG. 13 is a partially enlarged perspective view of an instrument for delivering a surgical thread according to another alternative of the present embodiment.

In this alternative, the outer cylinder 70 has an elliptical cross-section. The ellipse of the cross-section of the outer cylinder 70 has the minor axis parallel to the bending direction 26. As a result, the bending rigidity of the end 72 of the outer cylinder 70 is small in the bending direction 26 and is large in the direction 25 perpendicular to the bending direction 26.

In this alternative, the wall thickness varies by the circumferential position around the axial direction 24. The wall thickness of the outer cylinder 70 is larger at the portion intersecting with the major axis of the cross section and is smaller at the portion intersecting with the minor axis. As a result, the bending rigidity of the end 72 of the outer cylinder 70 is smaller in the bending direction 26 and is larger in the direction 25 perpendicular to the bending direction 26.

EXPLANATION OF REFERENCES

10: grip, 14: hernia gate, 16: hernia sac, 18: punctured portion, 20: base, 30: flat plate portion, 32: guide, 34: first rachet, 36: second rachet, 40: rising portion, 42: projecting portion, 50: needle position adjustor, 52: slit, 54: catch, 56: surface, 58: needle fixing portion, 60: loop opening and closing portion, 62: handle, 64: shaft, 66: hooking protrusion, 68: wire, 70: outer cylinder, 72: end, 80: hollow needle, 82: tip, 90: loop, 92: ligature

The invention claimed is:

1. An instrument for delivering a surgical thread, the instrument comprising:
   a grip;
   an outer cylinder fixed to the grip;
   a hollow needle extending inside the outer cylinder and being configured to be moved relative to the outer cylinder in a direction of an axis of the hollow needle; and
   a loop configured to be housed in the hollow needle, wherein
   an end of the outer cylinder is bent in a state where force is not applied,
   a bending rigidity in a bending direction of the outer cylinder is smaller than that of the hollow needle, and
   a bending rigidity in a direction perpendicular to the bending direction is larger than that enables to peel off peritoneum from extra peritoneal tissue by rotating around the axis.

2. The instrument for delivering a surgical thread according to claim 1, wherein a bending rigidity in the bending direction of the end of the outer cylinder is smaller than that in the direction perpendicular to the bending direction.

3. The instrument for delivering a surgical thread according to claim 1, wherein the outer cylinder has an elliptical cross-section of which minor axis is parallel to the bending direction.

4. The instrument for delivering a surgical thread according to claim 1, wherein the outer cylinder has an end face along the bending direction of the outer cylinder.

5. The instrument for delivering a surgical thread according to claim 1, wherein the hollow needle is configured to be fixed at least one axial position where a tip of the hollow needle is in the outer cylinder.

6. The instrument for delivering a surgical thread according to claim 1, wherein at least the end of the outer cylinder is colored.

7. An instrument for delivering a surgical thread, the instrument comprising:
   a grip;
   an outer cylinder fixed to the grip;
   a hollow needle extending inside the outer cylinder and being configured to be moved relative to the outer cylinder in a direction of an axis of the hollow needle; and
   a loop configured to be housed in the hollow needle,
   wherein an end of the outer cylinder is bent in a state where force is not applied,
   wherein a bending rigidity in a bending direction of the outer cylinder is smaller than that of the hollow needle,
   wherein a bending rigidity in a direction perpendicular to the bending direction is larger than that enables to peel off peritoneum from extra peritoneal tissue by rotating around the axis, and
   wherein a slit is formed on a side surface of the outer cylinder, the side surface being inner in a state where the end of the outer cylinder is bent.

8. An instrument for delivering a surgical thread, the instrument comprising:

a grip;

an outer cylinder fixed to the grip;

a hollow needle extending inside the outer cylinder and being configured to be moved relative to the outer cylinder in a direction of an axis of the hollow needle; and a loop configured to be housed in the hollow needle, wherein an end of the outer cylinder is bent in a state where force is not applied, wherein a bending rigidity in a bending direction of the outer cylinder is smaller than that of the hollow needle, wherein a bending rigidity in a direction perpendicular to the bending direction is larger than that enables to peel off peritoneum from extra peritoneal tissue by rotating around the axis, wherein the outer cylinder has an elliptical cross-section of which minor axis is parallel to the bending direction, and wherein wall thickness of the outer cylinder is smaller at portions intersecting with the minor axis of the elliptical cross-section than other portions.

\* \* \* \* \*